United States Patent
Reime

(10) Patent No.: US 9,606,084 B2
(45) Date of Patent: Mar. 28, 2017

(54) METAL DETECTOR FOR LOCATING METAL OBJECTS

(76) Inventor: Gerd Reime, Bühl (DE)

( * ) Notice: Subject to any disclaimer, the term of this patent is extended or adjusted under 35 U.S.C. 154(b) by 162 days.

(21) Appl. No.: 13/983,412

(22) PCT Filed: Feb. 2, 2012

(86) PCT No.: PCT/EP2012/000457
§ 371 (c)(1),
(2), (4) Date: Aug. 2, 2013

(87) PCT Pub. No.: WO2012/104086
PCT Pub. Date: Aug. 9, 2012

(65) Prior Publication Data
US 2013/0307532 A1 Nov. 21, 2013

(30) Foreign Application Priority Data
Feb. 2, 2011 (DE) .................... 10 2011 010 144

(51) Int. Cl.
*G01N 27/72* (2006.01)
*G01R 33/12* (2006.01)
*G01V 3/10* (2006.01)

(52) U.S. Cl.
CPC ............ *G01N 27/72* (2013.01); *G01V 3/107* (2013.01)

(58) Field of Classification Search
CPC .......... G01N 27/72; G01R 33/12; G01V 3/10; G01V 3/107
USPC ........... 324/239, 67, 225, 228, 233, 207.15, 324/207.12, 329, 326, 200, 207, 226, 232, 324/240, 241, 242, 243, 327; 331/65
See application file for complete search history.

(56) References Cited

U.S. PATENT DOCUMENTS

| | | | | |
|---|---|---|---|---|
| 3,777,256 A | * | 12/1973 | Harrison | 324/621 |
| 4,325,027 A | * | 4/1982 | Dykstra et al. | 324/329 |
| 4,470,015 A | * | 9/1984 | Hirschi et al. | 324/329 |
| 4,486,713 A | * | 12/1984 | Gifford | 324/329 |
| 5,045,789 A | * | 9/1991 | Inoue et al. | 324/225 |

(Continued)

FOREIGN PATENT DOCUMENTS

| DE | 10301951 A9 | 10/2004 |
|---|---|---|
| DE | 10318350 B3 | 12/2004 |

(Continued)

OTHER PUBLICATIONS

International Search Report for corresponding application PCT/EP2012/000457 filed on Feb. 2, 2012; Mail date Jan. 23, 2013.

*Primary Examiner* — Arleen M Vazquez
*Assistant Examiner* — Steven Yeninas
(74) *Attorney, Agent, or Firm* — Cantor Colburn LLP

(57) ABSTRACT

A method of locating metal or non-metal containing objects and materials includes regulating currents in at least two emission coils in relation to each other. A reception coil output signal is received by at least one reception coil or average values of demodulation phases generated from the reception coil output signal are regulated in relation to each other continuously to be zero even when exposed to metal. The amplitude(s) of the required controlled variables are detected as a value by demodulation, preferably at least at 0° and at a demodulation which is set off by 90° and are equalized, thereby allowing a reliable detection of an object to be detected even if other metal objects are present in the area of detection.

12 Claims, 15 Drawing Sheets

(56) References Cited

U.S. PATENT DOCUMENTS

| | | | |
|---|---|---|---|
| 5,691,640 A * | 11/1997 | King | 324/233 |
| 5,721,489 A * | 2/1998 | Weaver et al. | 324/329 |
| 5,729,143 A | 3/1998 | Tavernetti et al. | |
| 6,583,625 B1 | 6/2003 | Castle | |
| 8,063,777 B2 * | 11/2011 | Candy | 340/540 |
| 2008/0018331 A1 * | 1/2008 | Raulerson | G01N 27/9046 324/240 |
| 2008/0197835 A1 * | 8/2008 | Reime | 324/200 |

FOREIGN PATENT DOCUMENTS

| | | |
|---|---|---|
| DE | 102004047189 A1 | 4/2006 |
| DE | 102009009061 A1 | 7/2010 |
| DE | 102009021804 A1 | 11/2010 |
| DE | 102009029928 A1 | 12/2010 |
| WO | 2007012502 A1 | 2/2007 |

* cited by examiner

METAL DETECTOR FOR LOCATING METAL OBJECTS

CROSS-REFERENCE TO RELATED APPLICATIONS

The present application claims the priority of the German patent application 10 2011 010 144.6 which was filed on 2 Feb. 2011 and the published content of which is hereby expressly incorporated in the subject matter of the present application.

BACKGROUND OF THE INVENTION

The invention relates to a metal detector for locating metallic objects.

BRIEF SUMMARY

The advantage of the invention described here lies in a deliberate masking out of undesired metallic objects in the measuring zone and simultaneous detection of desired metallic objects. As an example, the detection of a relatively thin metallic piping in a wall behind a number of reinforcing steel members, reinforcing bars or reinforcement steel meshes (also referred to as structural steel) is shown in FIG. 1. FIG. 1 shows an object 1.1 in the form of a wall section incorporating embedded reinforcing steel members 1.2. A metallic piping 1.3 that is to be detected is located behind the reinforcing steel members 1.2. A metal detector 1.4 is guided past the object 1.1.

Although metal detectors in the state of the art would detect the reinforcing steel members unambiguously, the piping behind the reinforcing steel members would not usually be seen. Although in some circumstances one could deduce that a piping had been detected from an increase in the measured value in the region of the piping, a similar increase in the measured value also occurs if there was a further reinforcing steel member in place of the piping or if the reinforcing steel members are located closer together at one point. Reliable detection is not therefore possible with the known metal detectors.

In the case described above, the object of the invention is to completely mask the reinforcing steel members so that only the piping is seen exclusively.

In connection therewith, it is irrelevant how close together the reinforcing steel members or reinforcing bars are situated or whether they are located in front of, behind or beside the piping. In addition, the piping may consist of the same material as the reinforcing steel members that are to be masked out. The reinforcing steel members are only an arbitrary example. With the aid of the invention, virtually every possible metallic object can be masked out. Self-evidently, the effects of mineralised ground are also included.

Conversely, naturally, one can also deliberately seek for a particular object, whereby all other objects are then masked out. The object being sought must merely be of a shape or type of metal that differs from the objects that are to be masked out.

Furthermore, the object of the present invention is to improve a method for locating metallic objects and materials to the extent that reliable detection of an object requiring detection is also possible when other metallic objects are located in the detection zone.

It should be understood in the context of this application that "metallic" objects also include objects which contain only metal. An "object" in this application is to be understood as an object requiring detection which can, for example, be detected and which can be located in or behind other similar types of object or even objects differing therefrom such as walls or the ground and the like.

The basis of the invention is the patent application DE 10 2009 029 928 A1. A method is described therein in which, in a special coil arrangement, two oppositely regulated currents of two transmission coils continuously regulate out a received signal in a receiving coil arrangement to "zero". It is expressly pointed out that, in contrast to the state of the art, this process relates to one of continuous regulation to "zero", i.e. also in the case of metal approaching the coil arrangement 2.6.

In the state of the art, there are methods in which a received signal "zero" is produced without approaching metal. This is achieved e.g. by means of the mechanical alignment of the transmitting coil relative to the receiving coil, generally known as the "Double-D" arrangement of the coils (c.f. DE 103 01 951 A9). Or, two receiving coils are arranged within a transmission coil in such a way that the received signal is cancelled out (c.f. DE 103 18 350 B3). In order to get round the problem of mechanical tolerances, auxiliary windings in coil systems are also switched-in in order to achieve if possible a received signal "zero" without metal approaching (c.f. DE 10 2004 047 189 A1).

Thus, in all the methods described above, the received signal is always adjusted mechanically or electrically to "zero" without the influence of metal. The adjustment found without the influence of metal is retained when metal is exerting an influence. In these methods, an output signal of the receiving coil arrangement which is then evaluated accordingly does occur when metal is exerting an influence.

In contrast to the methods in the state of the art otherwise described above, the method underlying the present invention and described in DE 10 2009 029 928 A1 continuously regulates the received signal to "zero", i.e. in the case of metal approaching as well. An effect thereby arises of which the invention presented here makes use.

DETAILED DESCRIPTION

Figure 1:
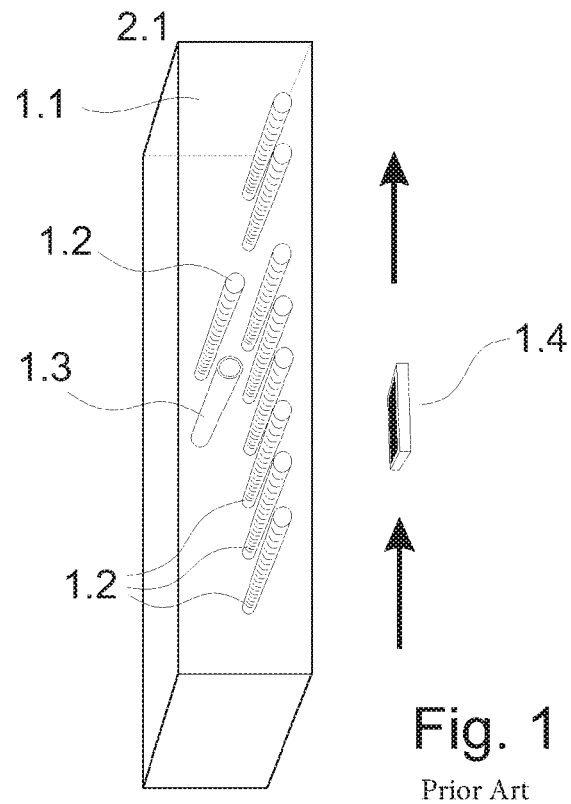
FIG. 1 shows a detection of a relatively thin metallic piping in a wall behind a number of reinforcing steel members.
Figure 2:
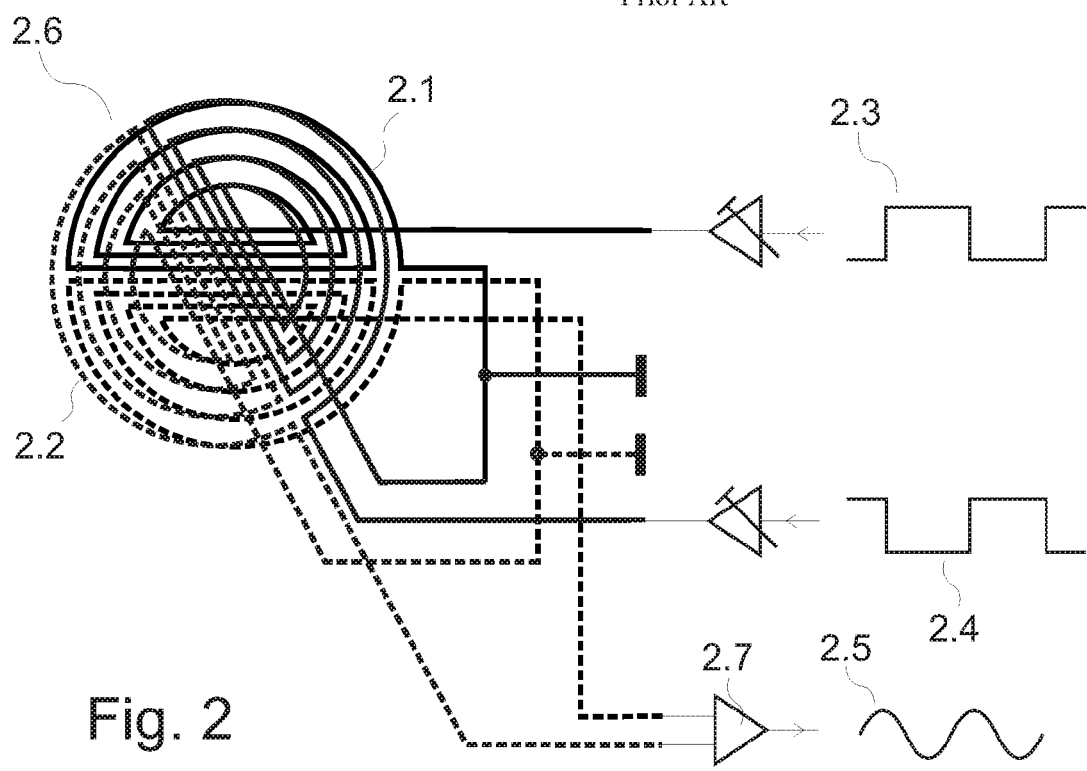
FIG. 2 shows a coil arrangement according to a non-limiting embodiment.

In order to understand this effect better, the special characteristics of the system must be described in more detail. FIG. 2 shows a coil arrangement 2.6 designed in accord with the technical teaching of DE 10 2009 029 928 A1. The transmission coil arrangement comprises two coils 2.1 and 2.2 and is fed by two mutually oppositely regulated currents 2.3 and 2.4. Coil 2.2 included in the coil arrangement 2.6 may also act as a receiving coil. Accordingly, the output signal of the receiving coil 2.2 is continuously stabilized to "zero" by means of the currents 2.3 and 2.4.

Figure 3:
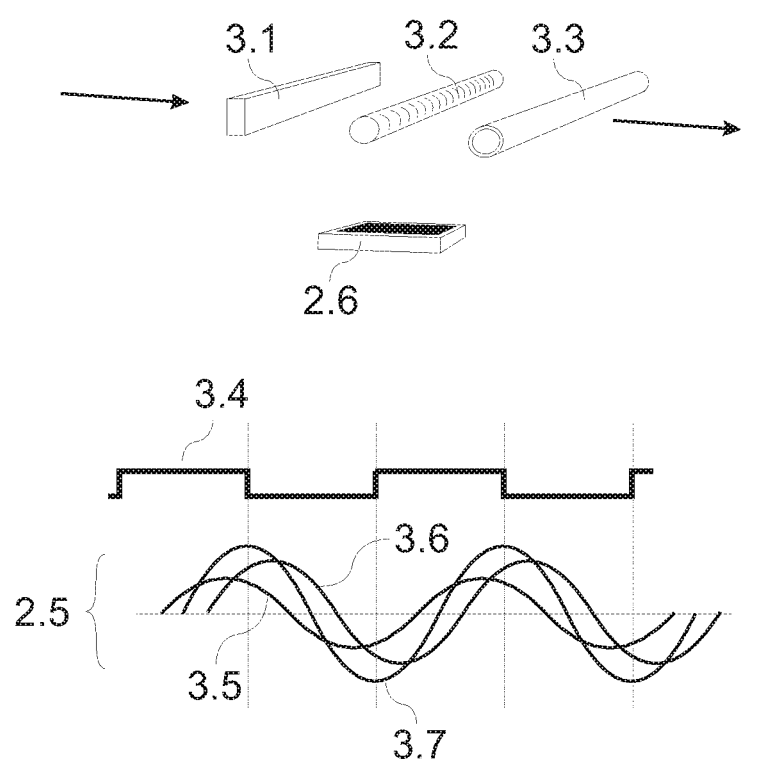
FIG. 3 illustrates the curves included in the signal of the receiving coil arrangement without the "regulation to zero" process in the presence of metal.

In order to better explain the present invention, the regulation process in the arrangement illustrated in FIG. 2 is now switched off and consequently, the two currents 2.3 and 2.4 are of the same magnitude. When metal approaches the coil arrangement 2.6, an output signal 2.5 therefore arises at the output of the preamplifier 2.7. FIG. 3 illustrates the ensuing signal 2.5 in somewhat more detail.

The curve 3.4 represents the square-wave current through the transmission coil arrangement 2.6 from DE 10 2009 029 928 A1, thus, in the case described, the currents through both transmission coils 2.1 and 2.2 are mutually inverted. In the present example, three different metallic objects are successively passed over the coil arrangement 2.6. For example, 3.1 is a metal bar having a square cross section, 3.2 is a reinforcing steel member and 3.3 is a metal pipe. Since the process of regulating "the received signal to zero" is switched off, there is a signal 2.5 at the output of the preamplifier 2.7 when approaching metal. This signal differs in amplitude and phase depending upon the type of metal or the geometry. As an example, three different signal curves 3.5, 3.6 and 3.7 for the three objects 3.1, 3.2 and 3.3 are illustrated in FIG. 3. This corresponds approximately to the state of the art excepting WO 2007/012502 A9, DE 10 2009 009 061 A1 and DE 10 2009 021 804 A1.

Figure 4:
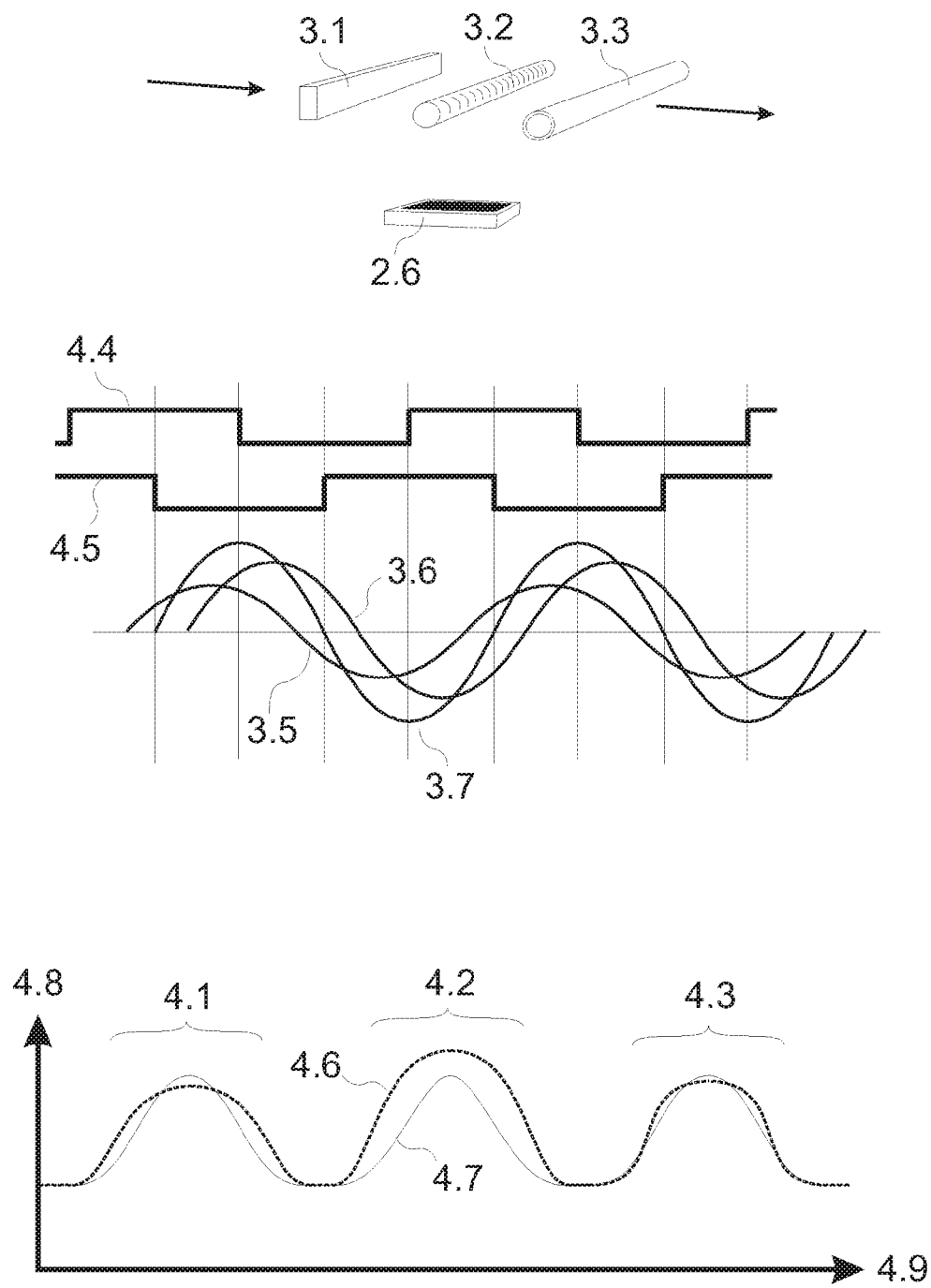
FIG. 4 illustrates changes in the phase and amplitude of the output signal of the preamplifier.

Methods are known in which an evaluation of the signal curves of the output signal of any particular coil arrangement takes place at e.g. 0° and 90° of the phase of the sending current. As a result, one then obtains two voltage values. An interpretation can then take place using these two voltage values, e.g. as to whether it relates to iron or a non-ferrous metal. It should be pointed out here that the depicted signal curves are only examples and could appear quite different depending upon the construction of the coil arrangement, the choice of clock frequency and the implementation of the electronic system. The fact remains that the curves differ depending upon the type of metal or the geometry. FIG. 4 clarifies what has been said above: the phase and amplitude of the output signal of the preamplifier changes for each of the objects 3.1, 3.2 and 3.3.

If the output signal of the preamplifier is synchronously demodulated at a rate of a demodulation clock 4.5, the signal waveform 4.6 results when the three objects mentioned above pass over the sensor for example. On the other hand however, if demodulation is effected by a second synchronous demodulator using the phase of the demodulation clock 4.4 shifted by 90°, this then results in the signal waveform 4.7.

The lower illustration in FIG. 4 shows the signal waveforms of the synchronous demodulation processes when the three objects 3.1, 3.2 and 3.3 are passed over the sensor. Here, the functioning of the synchronous demodulation process is assumed to be known. The signal waveforms 4.6 and 4.7 here designate the output signal of the respective synchronous demodulator.

Firstly, the metal pipe 3.3 is passed over the coil arrangement 2.6 as is illustrated in the upper part of FIG. 4. This, for example, results in the two signal waveforms for the 0° and 90° demodulation processes which are illustrated in section 4.3. For the same movement of the reinforcing steel member 3.2 or a reinforcing bar, the signal waveforms depicted in section 4.2 occur whilst the signal waveforms in the section 4.1 result for the metal bar 3.1. The type of metal detected can now be deduced from these two signal waveforms 4.6 and 4.7 if desired as is already known from the state of the art.

Figure 5:
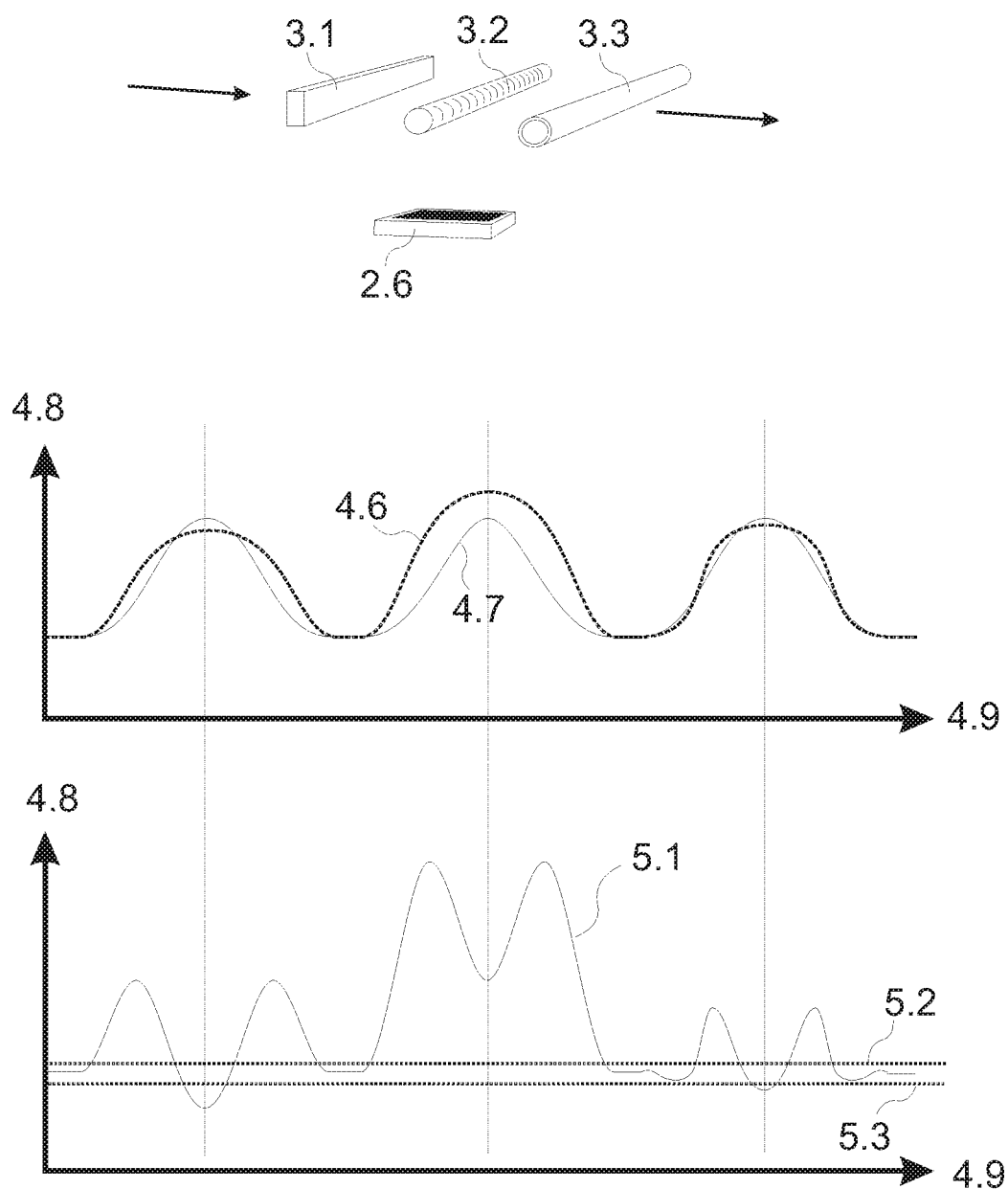
FIG. 5 illustrates a difference curve showing the formation of the difference between the signal waveforms.

One possible method for this purpose is the formation of the difference between the signal waveforms 4.6 and 4.7 as is illustrated by the difference curve 5.1 in FIG. 5. In the optimal position of the objects 3.1, 3.2 or 3.3 over the coil arrangement 2.6 as indicated here by the vertical dashed line, the e.g. upper threshold value 5.2 will be exceeded at times or the signal will fall below the lower threshold value 5.3 at other times. Naturally, this can be evaluated and a rough guide to the detected object, and in particular, to the type of metal can be obtained.

However, one can see immediately that if the object approaches the sensor unit laterally then the resultant signal waveforms become difficult to interpret. Consequently, these methods do not appear to be suitable for providing precise data concerning the detected object. In particular, the waveform of the curve 5.1 changes very markedly if e.g. the detected object is moved from the horizontal position into a vertical position.

The statements that have been made up to here basically refer to non-regulated transmission currents and an output signal of the receiving coil unit which is not continuously held at "zero" and thus basically reflect the state of the art. Now to the Invention:

The invention is now described exemplarily in more detail with reference to the accompanying drawings. Nevertheless, the exemplary embodiments are only examples which are not intended to restrict the inventive concept to a certain arrangement.

On the basis of the method proposed in DE 10 2009 029 928 A1 in which two transmission currents are regulated mutually oppositely in a special coil arrangement in such a way that a received signal of a receiving coil arrangement is continuously "zero", a method will now be described here which permits precise "masking" or "detection" of one or more specific metallic objects.

In the patent application mentioned above, the information about the presence of the metal is obtained from the regulating value which serves for stabilizing the receiving coil's output signal to "zero". Zero means that the average value of the demodulated signal in the first demodulation phase 6.1 is of equal magnitude to the average value of the second demodulation phase 6.2. The amplitude difference of the demodulated signal between the two demodulation phases is thus always held at "zero" by the process of regulating the currents in the transmission coils.

Figure 6:
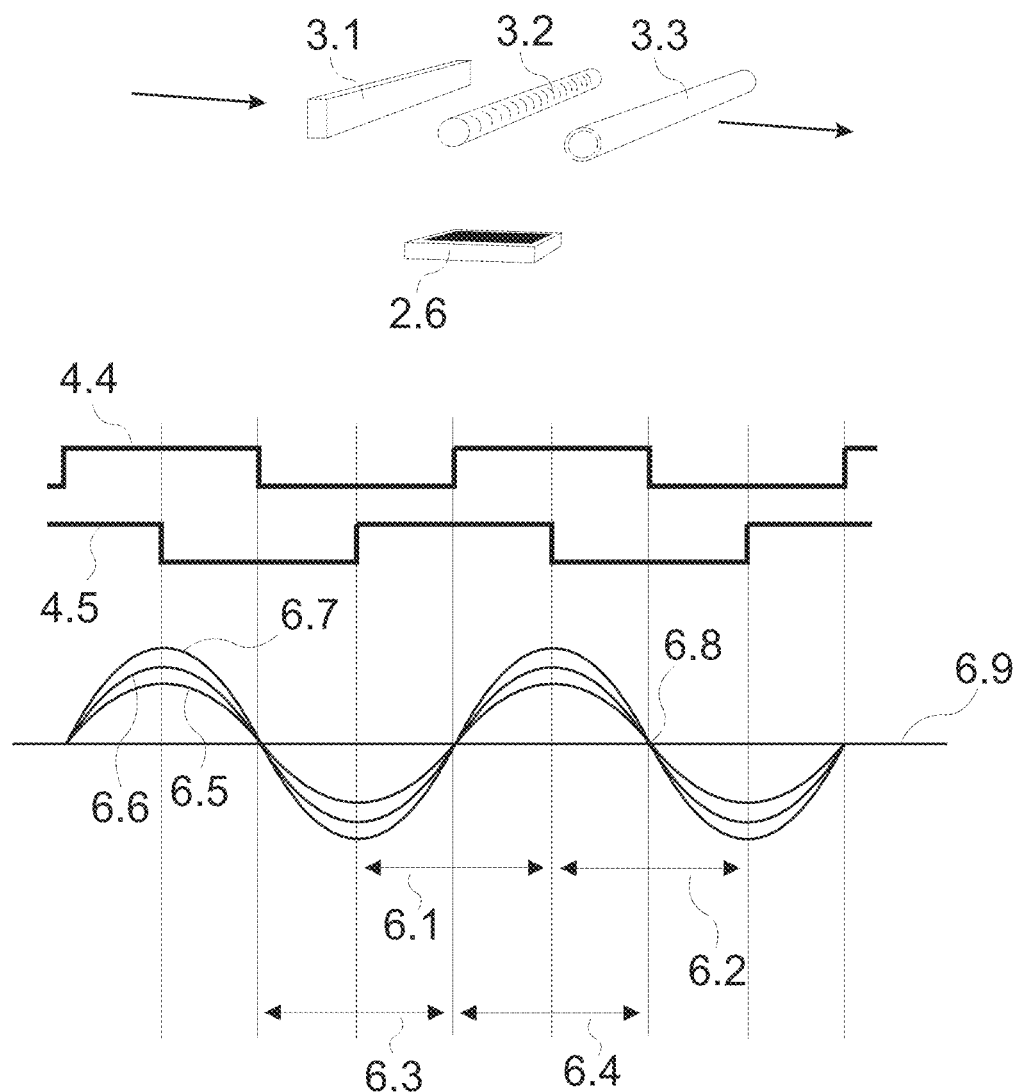
FIG. 6 illustrates the signal curves arising with the "centered" zero crossings due to a regulation process.
Figure 7:
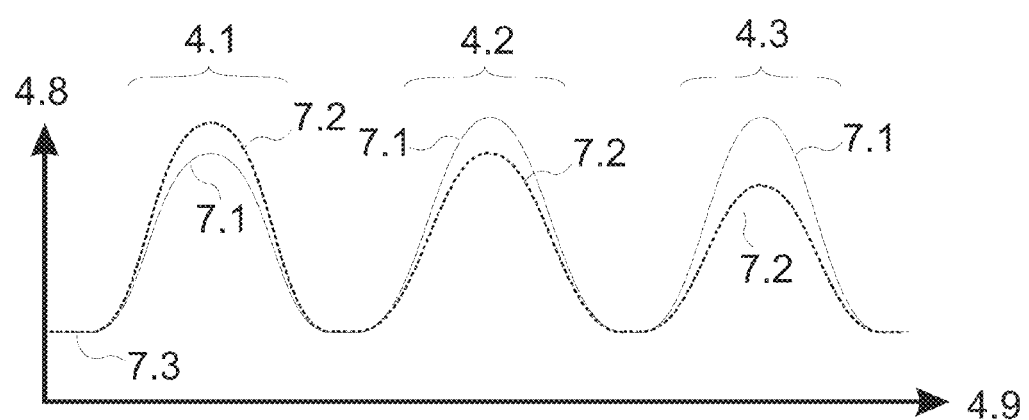
FIGS. 7 and 8 show the regulating value which regulates the currents of the transmission coils in such a way that a received signal in the receiving coil arrangement will be continuously "zero"
Figure 8:
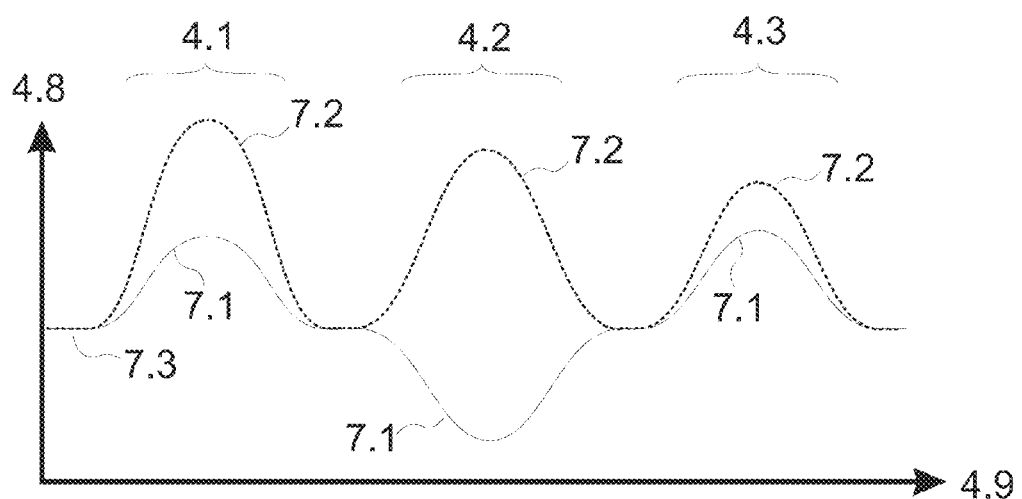

At this point, in order to avoid misunderstanding, it is best to go into more detail in regard to the signal curves in FIG. 4, FIG. 5 and FIG. 6. The illustration of the curves 3.5, 3.6 and 3.7 in FIG. 3 depicts the signal 2.5 of the receiving coil arrangement without the "regulation to zero" process in the presence of metal. This signal is again illustrated in FIG. 4. The curves 4.6 and 4.7 then show the signal 2.5 demodulated at 0 and 90 degrees. The curves 6.5, 6.6 and 6.7 show the signal appearing from the receiving coil arrangement after a process of stabilization to "zero" in the presence of metal. The curve 7.2 in FIG. 7 and FIG. 8 shows the regulating value which regulates the currents of the transmission coils in such a way that a received signal in the receiving coil arrangement will be continuously "zero". The curve 7.1 in FIG. 7 and FIG. 8 shows the signal 2.5 demodulated at the rate of the demodulation clock 4.4 in the presence of metal.

For clarification: The received signal of a clock cycle is preferably divided into about four preferably equal clock segments, i.e. switch-on time segments. In clock time, a plurality of clock cycles incorporating time segments that are clocked at the same clock rate by the clock generator 13.6 are generated.

Thus, without the presence of metal, no signal is present at the output of the preamplifier 2.7. The output signal corresponds to the line 6.9 in FIG. 6. Upon the approach of metal, a signal having zero crossings 6.8 that always fall exactly in the centre of the segments of the demodulation clock 4.5 can occur despite further correct stabilization to "zero" i.e., wherein the average values are always of the same magnitude in the segments of the demodulation clock 4.5 or the demodulation phases 6.1 and 6.2, or more explicitly, are always kept of the same magnitude by means of the current regulation process in the transmission coils. This signal can be measured by a second synchronous demodulator at a further demodulation clock 4.4 that is shifted in relation to the demodulation clock 4.5 by 90°.

To speak of "can" is done intentionally since the emergence of this signal is dependent on the phase shift of the received signal due to the type of metal and/or the geometry. The case can also arise that a phase shift of the received signal does not arise and thus too that there is no change in the value at the output of the second synchronous demodulator when approaching metal (certain types of metal or appropriate geometry). Thereby, the condition continues to remain that the average value of the preamplifier output signal 2.5 in the first demodulation phase 6.1 always corresponds to the average value in the second demodulation phase 6.2.

In the example again, the metal bar 3.1, a reinforcing steel member 3.2 and a metal pipe 3.3 successively pass over the coil arrangement 2.6. In the context of this application, it is to be understood that the term reinforcing steel member includes the different types of reinforcing bars and reinforcement steel meshes which are used in the building industry. FIG. 6 shows the signal curves 6.5, 6.6 and 6.7 then arising with the "centered" zero crossings 6.8 due to the regulation process. It should be noted that they all lie "over one another" in such a manner that they always have the common zero crossing 6.8 in precisely the same position and that the maximum and minimum amplitudes of the signal curves 6.5, 6.6 and 6.7 occur at the same time point.

In the next step, the received signal is demodulated with a signal of a demodulation clock 4.4 that is shifted by 90° with respect to the signal of the first demodulation clock 4.5. When the metal objects 3.1, 3.2 and 3.3 sweep over the coil arrangement 1.4, there thus arises e.g. a curve 7.1. Without the influence of metal, the curve has the quiescent value 7.3. (FIG. 7, FIG. 8). If one overlays this curve 7.1 with the regulating value curve for the regulation to "zero" process, then the astonishing effect is discovered that both curves change in a strictly equal manner with the approach of metal although with different amplitudes.

Depending upon the type of metal or the geometry, the amplitude of the curve 7.1 can also adopt negative values as the example in FIG. 8 shows. The same also applies under certain circumstances for the curve 7.2. For the sake of better understanding, the curve 7.2 was illustrated with a positive amplitude in all the illustrations in the event of approaching metal.

In a further step, the curve 7.1 is now multiplied by a value having positive or negative prefixes so that it is of equal size to the curve 7.2. This multiplier is preferably determined from the control variable or the control variables, e.g. from the ratio of the control variables. This can only happen if metal is present and a value for 7.1 or 7.2 occurs which is unequal to the quiescent value 7.3. The quiescent value 7.3 is designated by zero hereinafter and here, it describes the values which occur without metal being present. In principle, this step corresponds to an "amplitude regulating process" wherein the amplitude can be regulated or else inverted.

Figure 9:
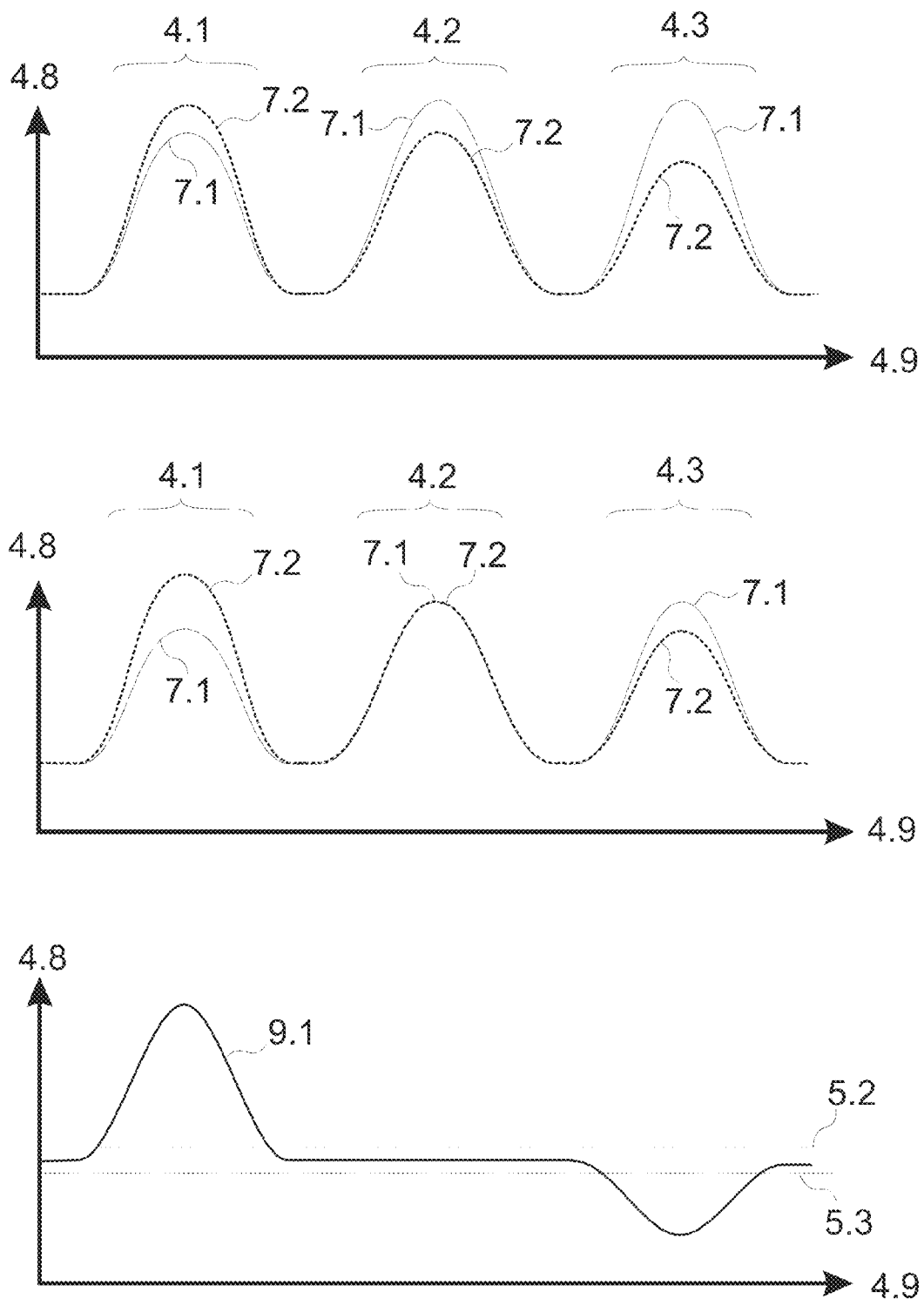
FIG. 9 illustrates a response of a signal associated with the coil arrangement as a metal object sweeps over the coil arrangement.

FIG. 9 summarizes the steps. In the upper illustration, the value 7.1 was not as yet regulated in amplitude. The values 7.1 and 7.2 still differ.

Figure 9A:
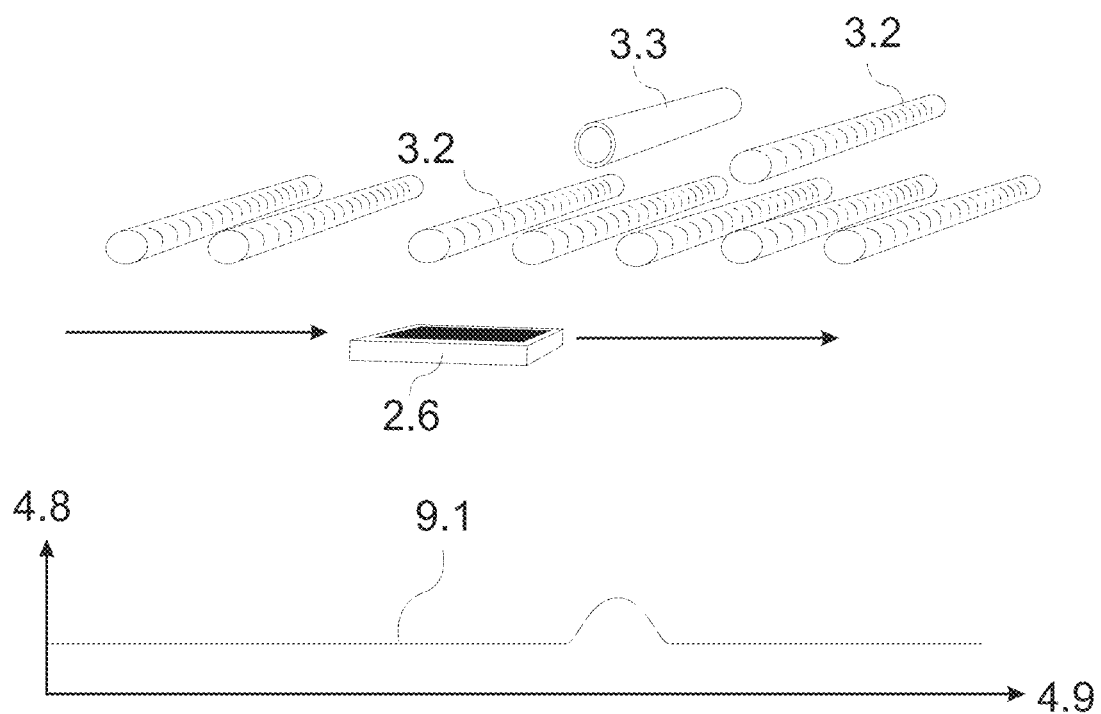
FIG. 9a shows the movement of an appropriate sensor along a number of arbitrarily arranged reinforcing steel members.

In the middle illustration, the value 7.1 has been multiplied by e.g. 0.9 so that the waveforms of the curves 7.1 and 7.2 coincide completely in the section 4.2. As a reminder: the reinforcing steel member was passed over the coil arrangement 2.6 in the section 4.2. The lower illustration now shows the difference value 9.1 of the curves 7.1 and 7.2. No difference is formed in the section 4.2 in which the reinforcing steel member 3.2 was passed over the coil arrangement 2.6. Surprisingly this also applies when the reinforcing steel member 3.2 is passed over the coil arrangement not only flat, but also perpendicularly thereto. If one provides the difference value with threshold values 5.2 and 5.3, then the process of sweeping over the coil arrangement 2.6 with the metal bar 3.1 or the metal pipe 3.3 can be detected accurately, whereas the reinforcing steel member 3.2 is "invisible". FIG. 9*a* shows the movement of an appropriate sensor 2.6 along a number of arbitrarily arranged reinforcing steel members. The reinforcing steel members lead to no change in the curve 9.1, it is solely the metal pipe 3.3 that is recognized.

In this case, "invisible" means that a single or several reinforcing steel members which are bundled, crossed or arranged at the most diverse angles and are at any distance from the sensor are not "seen", although e.g. a metal pipe in front, behind or beside the reinforcing steel members is detected accurately. And this also applies, if the metal pipe consists of the same material e.g. iron. Hereby, just one reinforcing steel member has to be "learnt" in order to mask a larger number of similar reinforcing steel members.

Consequently, in practice, a small coin can be detected accurately in 150 mm behind a double layer of closely packed 8 mm reinforcing steel members of structural steel. (Sensor: a coil arrangement from DE 10 2009 029 928 A1 having a diameter of 60 mm, the spacing of the reinforcing steel members from the sensor=50 mm, the spacing of a 20 EU-cent coin=150 mm)

The process of "making invisible" can now be accomplished for any metallic object, even e.g. metallised foils, mineralised ground etc. To this end, the sensor is brought to the object that is to be masked out, the curves 7.1 and 7.2 are made to coincide by an automatic equalising process (software) or by hand (potentiometer). Following this simple process, the said object becomes "invisible" to the sensor.

Figure 10:
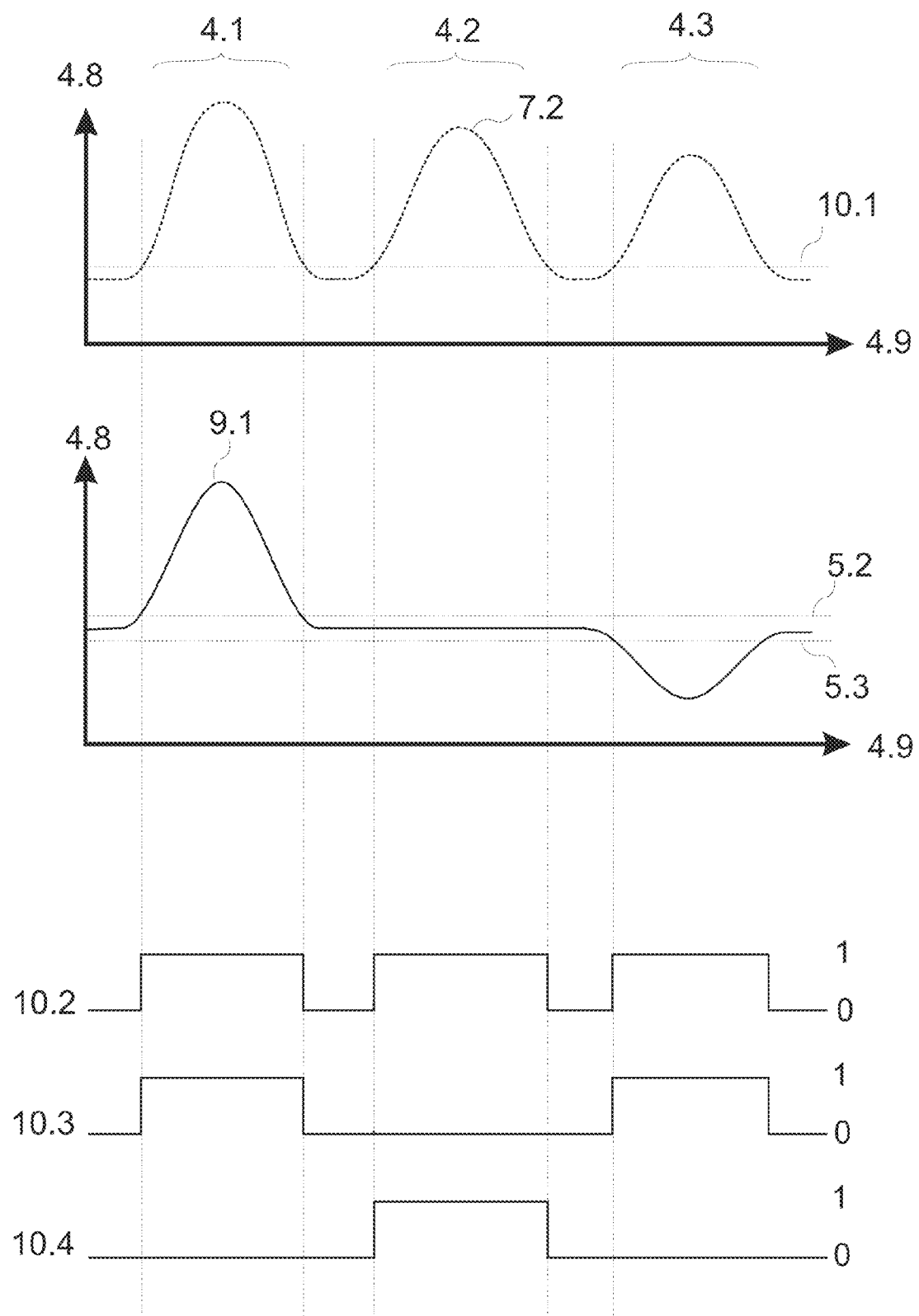
FIG. 10 illustrates the result of the digital evaluation of the signal curves.

Conversely, a deliberate search can naturally also be made for a specific metallic object using this arrangement. To this end, the curves 7.2 and 9.1 are evaluated by e.g. threshold values 10.1, 5.2 and 5.3. If the object that is to be sought, in the example again, the reinforcing steel member 3.2, has been learnt, i.e. the curves 7.2 and 7.1 made to coincide in the presence of the particular object, the curve 9.1 does not show any change when the said object approaches the sensor. In this case, neither of the threshold values 5.2 and 5.3 would be exceeded or fallen below. The curve 10.3 in FIG. 10 shows the result of the digital evaluation of curve 9.1. Whilst the square metal bar and the metal pipe led to a "1", the curve 10.3 remains on "0" when approached by the reinforcing steel member. A further evaluation of the curve 7.2 however shows all metallic objects represented as a "1" in curve 10.2. The curve 10.4 can be derived from the curves 10.2 and 10.3 by a simple logic circuit. This indicates the presence of the object that is to be sought whereas all other metallic objects are "invisible".

In the solution described above, the curve 7.1 was adapted to the amplitude of the curve 7.2. Self-evidently, in the converse case, the curve 7.2 can also be adapted to the amplitude of the curve 7.1. In both cases, the result of the difference formation processes, i.e. the curve 9.1, is the same. If the curves 7.1 and 7.2 are made to coincide by means of a given multiplier value automatically per software or manually e.g. by means of a potentiometer, this multiplier value serving as an identifier for a certain object from a table can, for example, designate the detected object in plain language. Multipliers and/or regulating values that have been determined earlier for example and for which the signals also coincide in the case of metallic contact can be stored in this table. This means: when the sensor sweeps past the three objects specified in the exemplary embodiment then the designations "metal bar, brass", "8 mm reinforcing steel member, structural steel", "30 mm piping, copper" could appear successively in a display for example.

Figure 11:
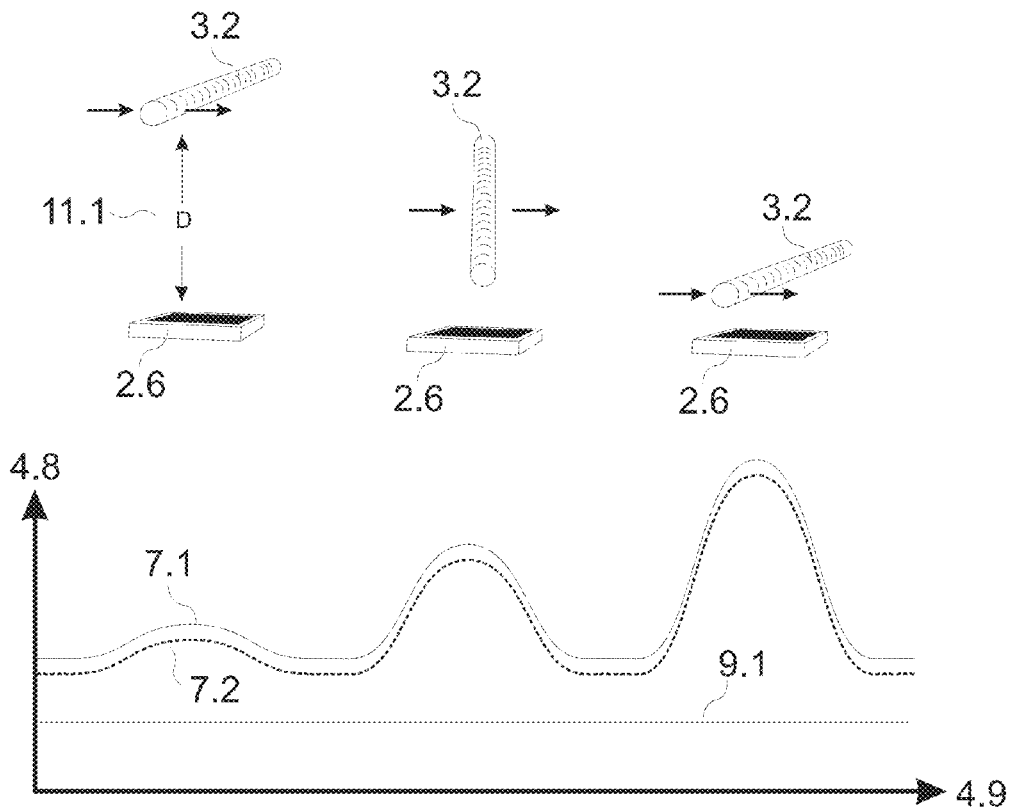
FIG. 11 shows the changes in the signal curves if the reinforcing steel member is passed over the sensor at different distances or positions.

Before Entering into Greater Detail in Regard to the Circuit Techniques Involved in the Solution, Yet Another Further Advantage of the Invention:

It is often desirable to be able to determine the depth of an object in the wall or in the ground. As already described above, objects can be recognized by their concrete designation, their specific multiplication values, i.e. their identifications so to speak, are stored in a memory of the detector device. This happens to a large extent in the invention described above independently of the distance of the object from the sensor. Self-evidently, it must lead to an evaluable change in value of the curve 7.1 or 7.2. FIG. 11 shows the changes in the curves 7.1 and 7.2 if, for example, the reinforcing steel member 3.2 is passed over the sensor 2.6 at different distances D (11.1) or positions. For better understanding, the curves 7.1 and 7.2 are illustrated separately in FIG. 11, in the practical case, they would be congruent. The difference 9.1 of the curves 7.1 and 7.2 then shows no change with movement of the reinforcing steel member over the sensor 2.6.

If, in the exemplary embodiment, the reinforcing steel member were to be recognized, then the depth or the distance, sensor to reinforcing steel member, can now be determined from the necessary change in the amplitude of the curve 7.1 and by means of a corresponding conversion value stored in the table for "reinforcing steel members".

Figure 12:
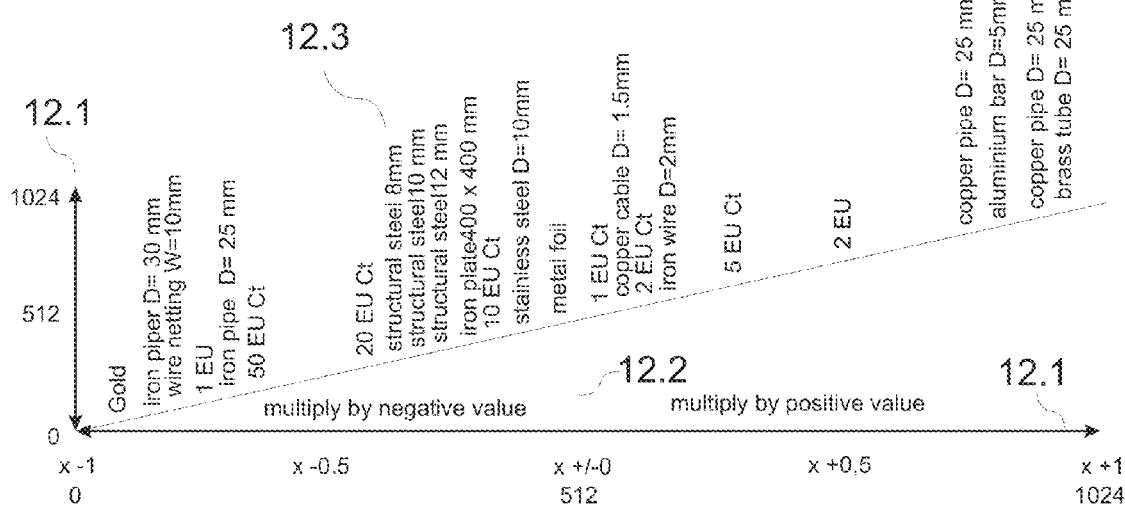
FIG. 12 shows the process of determining the depth or distance from the necessary change in the amplitude of the signal curves.

FIG. 12 shows the example of such an evaluation process. For the sake of simplicity, one proceeds on the assumption of a digital regulation of the amplitude of the signal 7.1. The regulating range is intended to be effected over 1024 steps. No change in the value of the curve 7.2 occurs in half of the regulating range, i.e. by step 512. The value 0 represents a multiplication by minus 1, 1024 then corresponds to a multiplication by plus one. Larger or smaller maximum multiplication values could also be used in dependence upon the design of the electronics. The only essential thing is that the two curves 7.1 and 7.2 can be set to coincide. The multiplication values from "multiplication by minus one" (x (−1)), past the neutral multiplication value 12.2 up to the "multiplication by plus one" and the metal objects 12.3 which cause the difference 9.1 of the curves 7.1 and 7.2 to become zero with the appropriate multiplication factor are presented on the line 12.1. One has had to dispense with a scale diagram in the illustration in FIG. 12, but it provides a rough overview of some known metal objects including coins in common use in Europe.

Consequently, if a difference of the curves 7.1 and 7.2 falls to zero at a certain multiplication value, the object corresponding to the multiplication value can be assigned from a table.

Circuit Embodiment:

The following description describes just one exemplary embodiment, differing circuit variants could also be used. The only important thing is that metallic objects can be masked out or intentionally detected by using the described method.

The prerequisite is a circuit which affects the currents of the transmission coils 13.2 and 13.3 in such a way that they achieve a state in the one or more receiving coils 13.4 in which the output signal of the coils 13.4 or the output signal 2.5 of a downstream preamplifier 2.7 becomes "zero" with and without the presence of a metal. Zero means the average value of the demodulated signal e.g. using synchronous demodulation in the first demodulation phase 6.1 is equal in size to the average value of the second demodulation phase 6.2. The amplitude difference of the demodulated signal between the two demodulation phases is thus always held at "zero" by the process of regulating the currents in the transmission coils.

Figure 13:
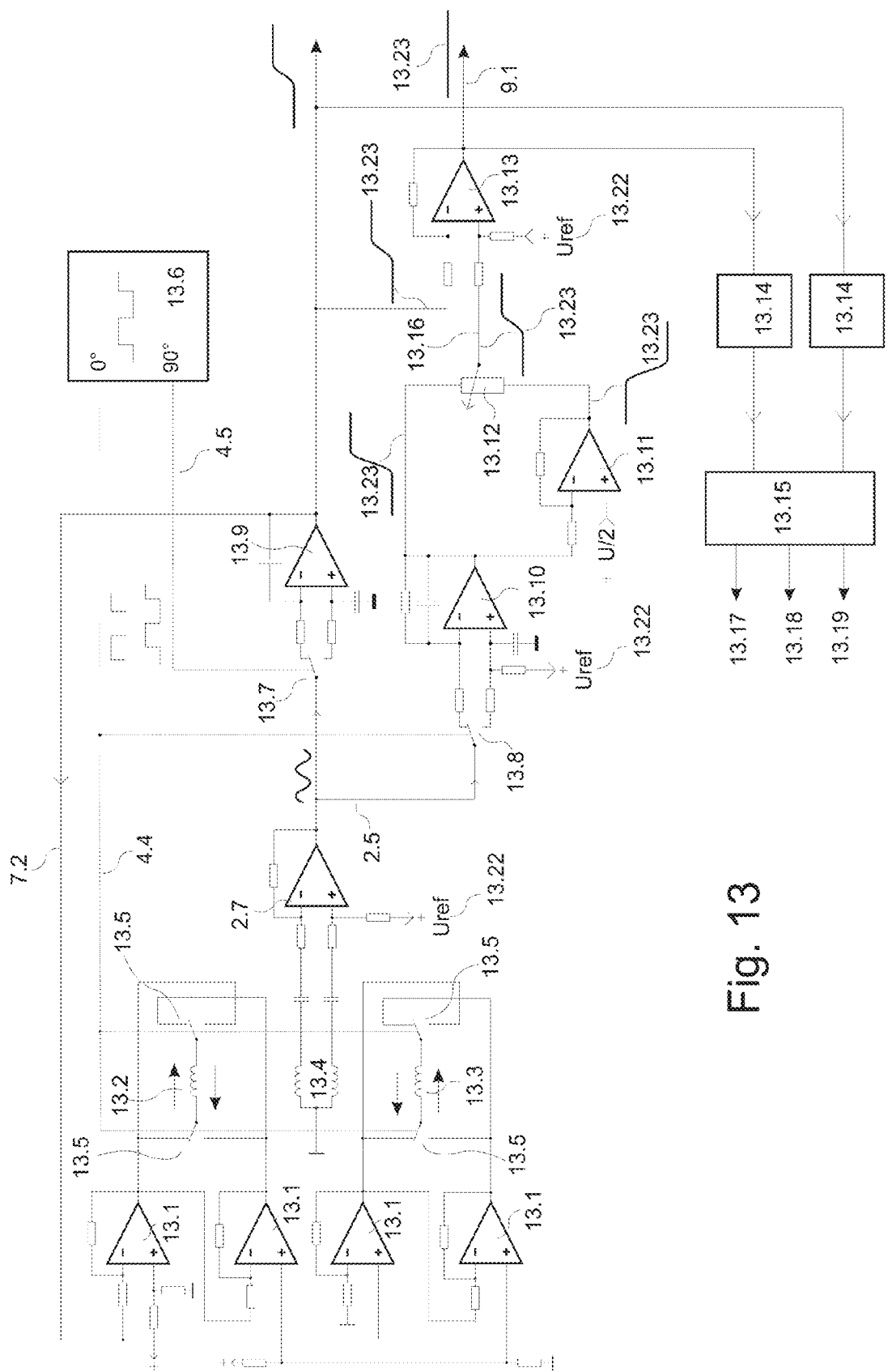
FIG. 13 illustrates a circuit diagram for detecting metallic objects according to a nonlimiting embodiment.

To this end in the exemplary embodiment in FIG. 13, the switches 13.5 are controlled by the demodulation clock 4.4 in such a way that the current through the coils 13.2 and 13.3 changes direction in synchronism with the clock. The clock frequency can be selected at will, e.g. 100 kHz. The voltage needed for a certain current is provided by the operational amplifiers 13.1. These in turn are controlled by the regulating value 7.2 in such a way that the current through the transmission coils 13.2 and 13.3 is of the same magnitude for a given regulating value 7.2. When the regulating value 7.2 changes in one direction, the switched current in the first transmission coil 13.2 rises for example whereas it falls in the second transmission coil 13.3. When the regulating value changes into the other direction, the current in the first transmission coil 13.2 falls, whilst it rises in the second transmission coil 13.3. It is thereby ensured that the clocked current flows in the transmission coils 13.2 and 13.3 can always be regulated relative to each other by the regulating value 7.2 in such a way that the received signal of the coils 13.4 or the output signal 2.5 of the amplifier 2.7 is continuously at "zero".

The demodulation clock 4.4 is supplied by the clock generator 13.6 and designated in the exemplary embodiment by the phase "0°" and it controls the change-over switches 13.5 for the coil current. A further demodulation clock 4.5 displaced by 90° controls a first switch 13.7 for a first synchronous demodulation process. It is irrelevant as to which of the signals of the demodulation clock 4.4 and 4.5 is designated by "0°" or "90°", what is important is that the phase shift of the demodulation clock 4.4 and 4.5 preferably amounts to 90°.

13.9 is a high-gain comparator for the output signals of the amplifier 2.7 that are switched at the rate of the demodulation clock 4.5. Consequently, the averaged signal components located in the positive clock phase are compared with those located in the negative clock phase. In this case, "high-gain" means that even the smallest deviations of the averaged signal components located in the clock phases lead to a significant deviation of the regulating value 7.2. In practice, the DC amplification of this stage is greater than 120 dB.

In the stabilized state, the output signal of the amplifier 2.7 then corresponds to the curve 6.9 in FIG. 6 or the signal curves 6.5, 6.6 and 6.7 when affected by metal. The zero crossing 6.8 is always in precisely the same place due to the continuous regulation process.

A further switch 13.8 for a second synchronous demodulation process which is shifted by 90° relative to the first is controlled at the rate of the demodulation clock 4.4. The averaged signal components located in the positive clock phase are compared with those located in the negative clock phase thereby. In contrast to the comparator 13.9, the comparator 13.10 only has a moderate amplification factor, e.g. two-times. The output signal of the comparator 13.10 is illustrated in FIG. 7 as curve 7.1. Without the influence of metal, the output signal of the comparator has the quiescent value 7.3. Depending upon the type of metal or the geometry, it can deviate to a greater or lesser extent in the one or the other direction under the influence of the metal. The output signal of the comparator 13.10 is now passed on to the terminals of a regulator 13.12 directly on the one hand and inverted by the inverting stage 13.11 on the other. The output signal of the comparator 13.10 can be regulated in magnitude and with arbitrary prefix signs thereby.

Following these measures, a regulating value 7.2 and a value 13.16 which is adjustable in amplitude and prefix sign is now available. Both values will alter markedly and uniformly under the influence of metal even at various distances but they may possibly change with differing amplitudes. The upper illustration in FIG. 9 clarifies this. Hereby, the curve 7.1 corresponds to the still unregulated curve 13.16.

The regulating value 7.2 and the value 13.16 are supplied to the differential amplifier 13.13. Without the influence of metal, the regulating value 7.2 and 13.13 have no difference so that there is no difference information on the output of the differential amplifier 13.13. In the exemplary embodiment, the output value then corresponds to the reference voltage 13.22 or the curve 9.1.

Now if a certain object, e.g. a reinforcing steel member, is to be masked out during the metal detection process, this object is first brought into the proximity of the metal detector. As a rule, the output value 9.1 at the output of the differential amplifier 13.13 will thereby change, i.e. it becomes unequal to the reference voltage 13.22. The value 13.16 is now varied by the regulator 13.12 until such time as the output value 9.1 again corresponds to the reference voltage 13.22.

FIG. 11 shows the two curves of the values 7.1 and 7.2. Curve 7.1 then corresponds to the regulated value 13.16. The values of the two curves are always the same even when the metal object is at different distances so that no difference curve 9.1 will occur for the object that is to be masked out. Consequently, this metal object is not recognized. The curves 13.23 in FIG. 13 illustrate the above statement. All other metal objects however lead to an inequality of the difference value 9.1 from the reference voltage 13.22.

This inequality can now be determined e.g. by threshold values. This is illustrated in the lower illustration of FIG. 9. The difference value 9.1 exceeds the upper threshold value 5.2 during the approach of the metal bar 3.1 and falls below the lower threshold value 5.3 during the approach of the metal pipe 3.3. By contrast, the approach of the reinforcing steel member 3.2 does not lead to a change of the difference value 9.1.

It has been established that a plurality of objects that are to be masked out are also masked out by means of this method even if only a single one of these objects has been learnt. In practice, this means: only one reinforcing steel member has to be learnt in order to also mask a bundle of several reinforcing steel members. Even sweeping over just the end of the reinforcing steel member is masked out accurately. By contrast, all other metal objects, whether larger or smaller than the object that is to be masked out are recognized.

For example, if a coin at a distance of 15 cm leads to a certain value 9.1, then this value will not alter even if one or a bundle of reinforcing steel members is moved between the coin and the sensor or laterally thereof or behind the coin.

In the exemplary embodiment, the output value of the comparator 13.10 was regulated. However, the regulating value 7.2 could also be regulated. Alternatively or else both. It depends only on the fact that, in the case of the "learnt" object, the input values of the differential amplifier 13.13 are of the same magnitude.

In the exemplary embodiment of FIG. 13, the two values 7.2 and 9.1 are supplied to the respective threshold switches 13.14. Their outputs are interlinked in a further simple logic circuit in such a way that there results
an output value 13.17 for "all metal objects",
an output value 13.18 for "all metal objects with masking of unwanted objects" and
an output value 13.19 for "only sought" (=masked out) objects.

With the aid of an appropriate evaluation process, conclusions can also be drawn in regard to the type of metal that has been detected from the output value of the comparator 13.10. Naturally, the method described can not only completely mask metallic objects such as the example of "reinforcing steel members". It is also outstandingly suitable for the suppression of so-called "ground effects" of mineralised ground.

In the exemplary embodiment, the clock value 0° was used for the control of the coil currents in the transmission coils 13.2 or 13.3 and for a first demodulation process, and a clock value shifted by 90° for a second demodulation process. Depending upon the implementation of the circuit, a clock value deviating from 0° could also be used. Preferably however, the relative displacement of the two demodulation clock values will amount to 90°. Furthermore, the respective average value of the signal 2.5 was used during the respective clock phase in the exemplary embodiment. In addition, with appropriate sinusoidal shaping of the received signal 2.5, a brief sampling process (sample+hold) at appropriate time points will adequately suffice. Sinusoidal shaping can be achieved e.g. by a resonance condenser on the receiving coils 13.4.

If a specification of the detected objects with corresponding depth data is wished, then a µP based solution would probably be useful. An example should clarify the functioning:

A metal detector produced in accord with the method described above is moved along a wall. If it detects metal, then the following representation can appear in an appropriate display for example: copper piping, diameter 30 mm, depth 70 mm. The metal detector is moved on further, upon detecting further metal there appears e.g. structural steel, diameter 8 mm, depth 55 mm etc. Since many known objects such as e.g. structural steel having a diameter of 8, 10 or 16 mm have specific, but differing "correcting factors" for the value 13.16, these can be stored in a memory. The same applies, for example, to various pipes, current conductors etc.

In the simplest case, upon detection of metal, the regulator 13.12 that is replaced in a solution based upon a µP by a mathematical function is altered until such time as the output value 9.1 adopts the value 13.22 i.e. until "no metal detection" is reached. The value of the mathematical function necessary for this then corresponds to an "object", e.g. 8 mm structural steel which was previously stored for this value so that this information can also appear in the display.

The regulating value 7.2 is determined in parallel therewith. This value is proportional to the distance and can be converted directly into a cm spacing for example.

Figure 14:
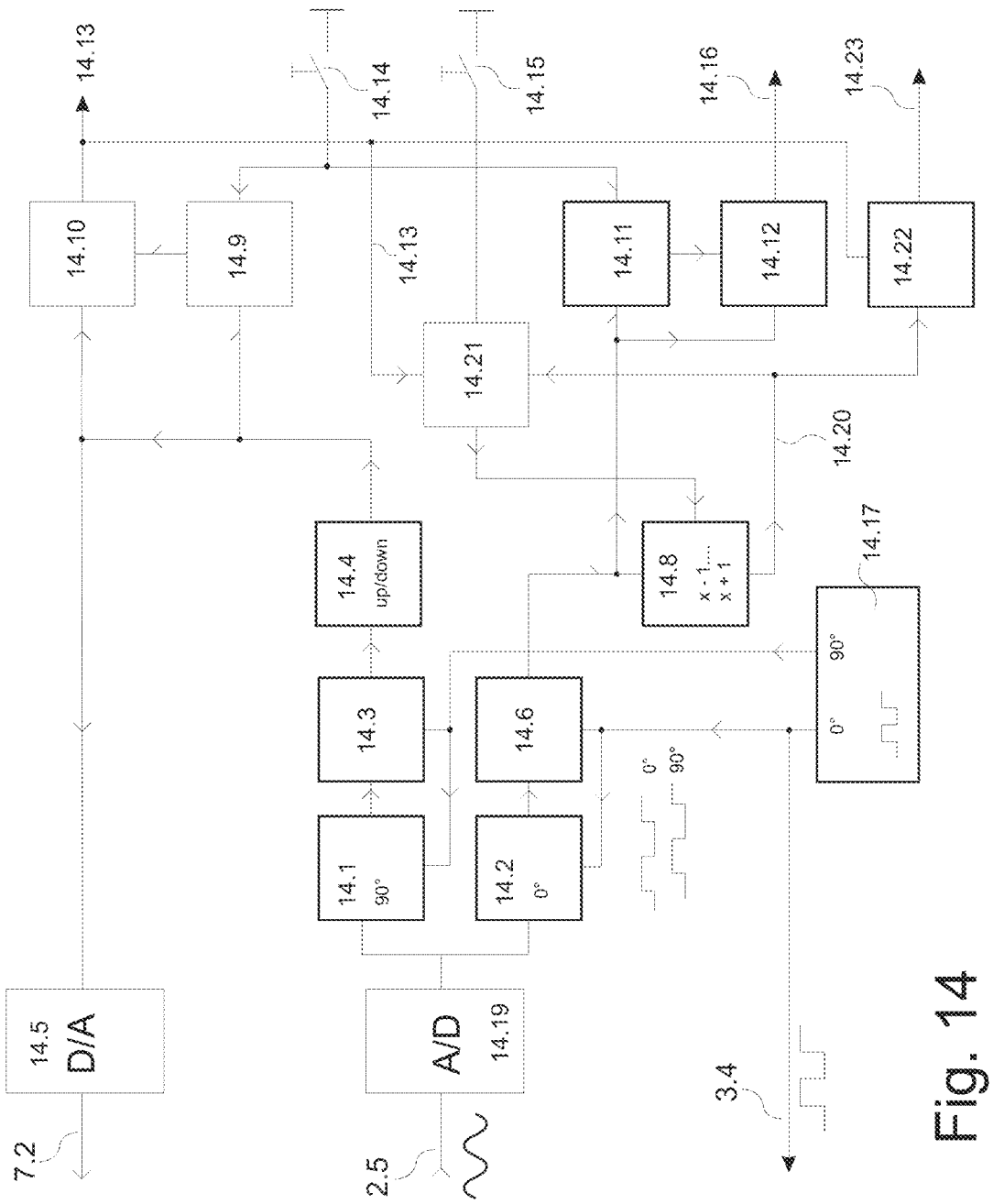
FIG. 14 illustrates a circuit diagram for detecting metallic objects with corresponding depth data according to a nonlimiting embodiment.

FIG. 14 shows an exemplary embodiment of a µP based solution. The output signal 2.5 of the preamplifier is supplied to the analogue-digital converter 14.19. A first digital averaging process 14.1 forms the average value for each clock phase with a phase shift of 90° with respect to the transmit clock 3.4. The digital comparator 14.3 compares the average value in the positive clock phase with respect to the average value in the negative clock phase. The result is supplied to an up/down counter 14.4. The counting state is converted in the D/A converter 14.5 into an analogue value which, as a regulating value 7.2, controls the currents in the transmission coils 13.2 and 13.3. The counter 14.4 counts either up or down in each clock phase until such time as a stable state of the regulation process is established and the signal 2.5 corresponds to the illustration in FIG. 6. Thus, without the influence of metal, there is no output signal in accordance with the curve 6.9, but with the influence of metal, there results curves such as 6.5, 6.6 or 6.7 for example. Again, the important factor here is that the zero crossing 6.8 always occurs in exactly the same place, for example, at the change of clock signal from demodulation clock 4.4. On depressing the key 14.14, the current count value is read out from the counter 14.4 into a first value memory 14.9. This can happen in a situation without the influence of metal for example. In the difference forming circuit 14.10, the difference of the stored counter value without the influence of metal and the current value e.g. with the influence of metal, is determined and is sent out as an approach value 14.13 of any metal object. In other words: key 14.14 implements an equalisation process without the influence of metal in order to compensate for possible inaccuracies in the electronic system or the coil system.

In a second digital average-forming circuit 14.2, the average value of the signal 2.5 is determined at the clock phase 0°. The clocked inverting stage 14.6 changes the prefix sign of the average value at the clock rate 3.4 so that the output value corresponds to the output value of a conventional analogue synchronous demodulator. The "shape of the curve" of the digital output values for different metal objects resulting thereby corresponds to the curve 7.1 in FIG. 7 or FIG. 8. The output values mentioned above are supplied to the multiplication stage 14.8 and to a second value memory 14.11. The output value of the inverting stage 14.6 was stored in the value memory 14.11 by depressing the key 14.14 during the situation without the influence of metal (see above). In the difference forming circuit 14.12, the difference of the stored value and the current value under the influence of metal for example is determined and delivered as a material identifying value 14.16. For example, information about the metal object is contained in this value, the value deviates in one direction in the case of iron and in the other direction with non-ferrous metal for example.

The multiplication stage 14.8 can reduce or amplify or even invert the output value of the inverting stage 14.6 in an arbitrary manner. To this end, on depressing the key 14.15, the output value 14.20 that has been manipulated in terms of its amplitude or polarity under the influence of metal is compared with the current value 14.13 in the comparator stage 14.21. In the case of deviation, the comparator stage 14.21 regulates the multiplication stage until such time as the value 14.20 and the value 14.13 are exactly the same magnitude. This is illustrated in FIG. 11. For the purposes of making the synchronisation of the two curves easier to appreciate, they were illustrated as being displaced. In practice however, they are precisely superimposed.

The metal object was "learnt" by virtue of this measure. When approaching the learnt object, the changes in value of the values 14.13 and 14.20 behave in the same manner. In the case of all other metal objects, the values 14.13 and 14.20 do also change, but in a different manner.

In order to recognize these other metal objects unambiguously, the values 14.13 and 14.20 are compared in the difference forming circuit 14.22 and the difference value is then passed on as an output value 14.23. This output value 14.23 now contains the masking of the learnt object.

Figure 15:
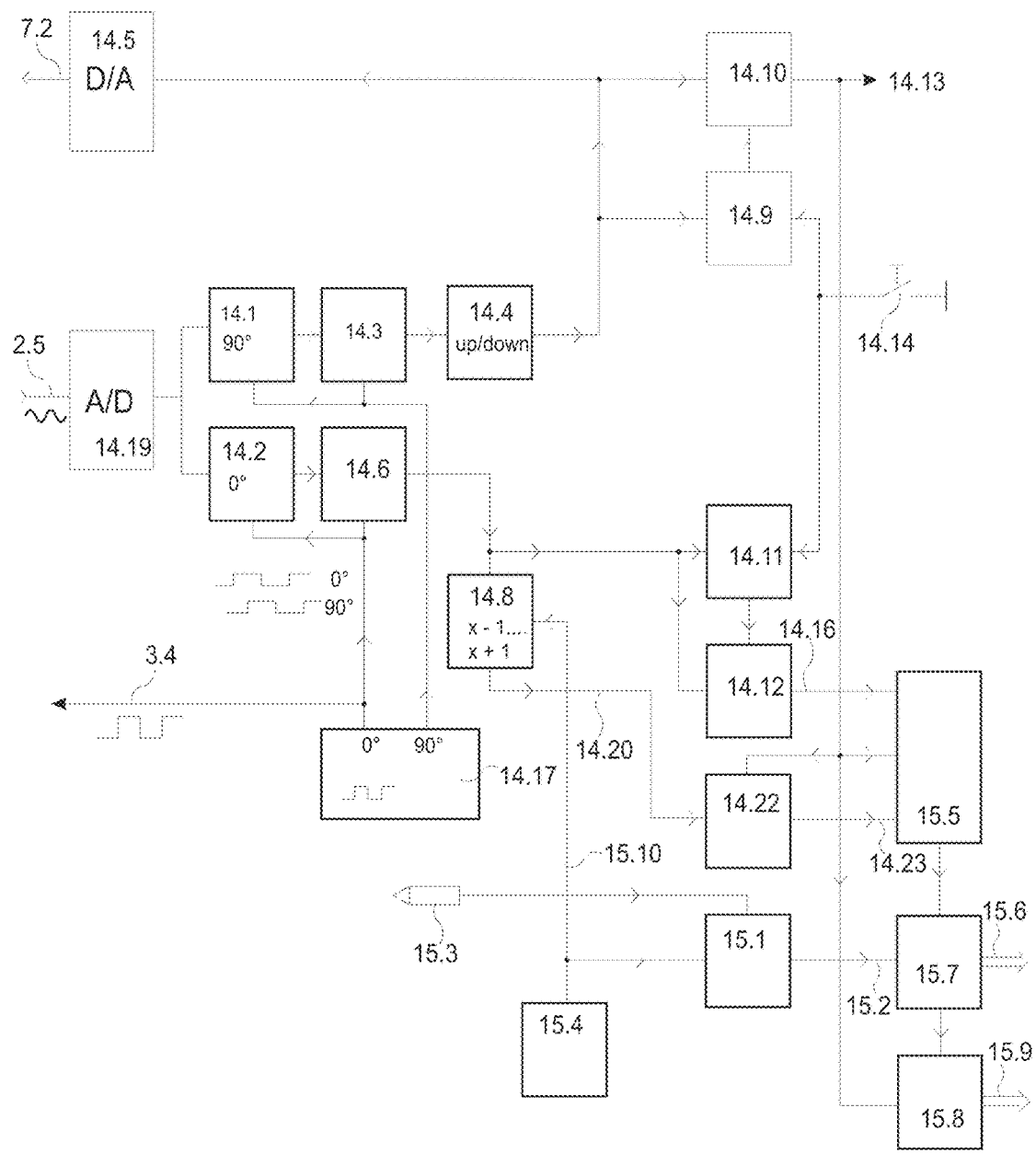
FIG. 15 illustrates a circuit diagram for detecting metallic objects according to a nonlimiting embodiment

Conversely, a particular object can naturally be deduced from the values 14.13, 14.16 and 14.23. This is achieved in that the multiplication stage 14.8 regularly calculates all possible multiplication values. To this end in the exemplary embodiment in FIG. 15, a multiplication value generator 15.4 supplies the corresponding multiplication values 15.10. Thus, for example, the entire range of values of the multiplication stage 14.8 can be swept through every 20 ms. In the presence of metal, a state will thereby be reached for at least one multiplication value 15.10 in which the output value with masking 14.23 (corresponding to curve 9.1) is zero, whilst the approach value for any particular metal object 14.13 and the material identifying value 14.16 is not equal to zero. This corresponding value 15.10 can then be assigned in a table which contains a number of generally known objects such as 8 mm structural steel or 25 mm copper pipe etc. for example. In practice, over one hundred different objects could be identified in this way.

Since the magnetic properties of a metal object are temperature-dependent, a temperature sensor which measures the ambient temperature or the temperature of the detected metal object can add on an appropriate correction factor to the multiplication value 15.10. The corrected value 15.2 now corresponds to the identification value for a particular metal object which is retrieved from the plain language memory 15.7 and expressed in plain language 15.6 for example. The enabling process for the plain language output is effected by means of the logic circuit 15.5 from the values 14.13, 14.16 and 14.23 only upon detection of metal.

If a particular metal object has been recognized, the distance to the detected object can also be expressed in plain language 15.9 by evaluating the approach value 14.13 in a further value allocation stage 15.8. The two last-mentioned plain lan-guage outputs can then control a display, on which the detected object is then represented in the form of text or an image together with an indication of the depth.

The invention described is also suitable for analysing material or for quality control processes in the sheet metal working field for example since even the smallest changes in the composition of the material are detected accurately.

Moreover, the coil arrangement is not limited as in the exemplary embodiment to just two transmission coils with receiving coil/s, more than two transmission coils can also interact with more than two receiving coils in order to form a whole coil array for example.

At least two current-regulated transmission coils thereby act on one or more receiving coils in such a way as to result in a "zero" signal. "Zero" means that nothing other than noise is detected. This relates to the state without metal, the average value of the demodulation phases is the same i.e. always mutually "zero" with metal. However, there is a resultant signal with a phase shift of 90°, and this average value of the demodulation phases is mutually not equal to "zero". Thus, when one speaks of "continuous regulation to zero", then the average values of the demodulation phases are mutually "zero", even under the influence of metal.

In the previous exemplary embodiments, only the coil currents of the two transmission coils 2.1 and 2.2 were mutually regulated in such a way that the average values of the output signal of the differential amplifier 2.7 were of the same magnitude during the first demodulation phase 6.1 and the second demodulation phase 6.2. Consequently, a clock synchronous signal could be formed in the third demodulation phase 6.3 and the fourth demodulation phase 6.4. The regulating value 7.2 and the amplitude value in the clock phases 6.3 and 6.4 were used for the purposes of evaluating the metal detection process.

Figure 16:
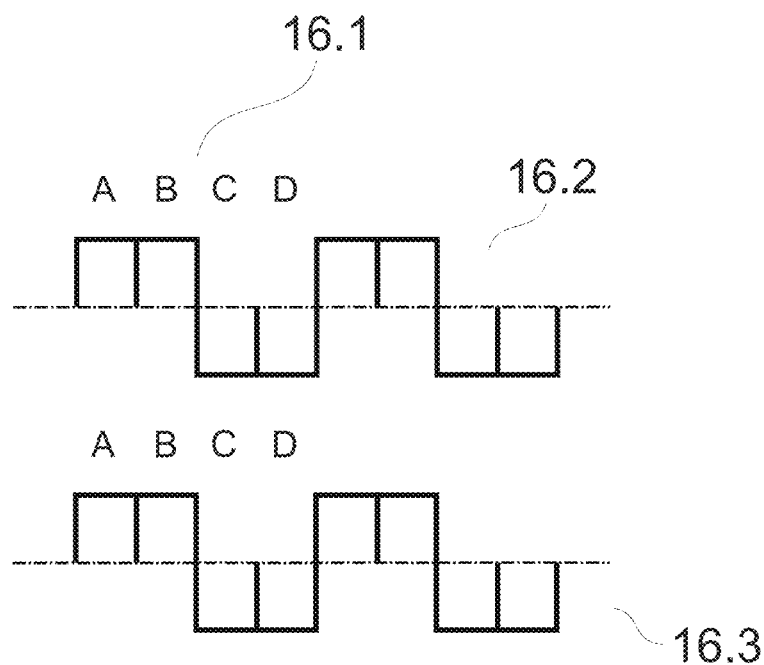
FIG. 16 illustrates the division in time of feed current segments associated with of a transmission coil without influence from one or more metallic objects.
Figure 18:
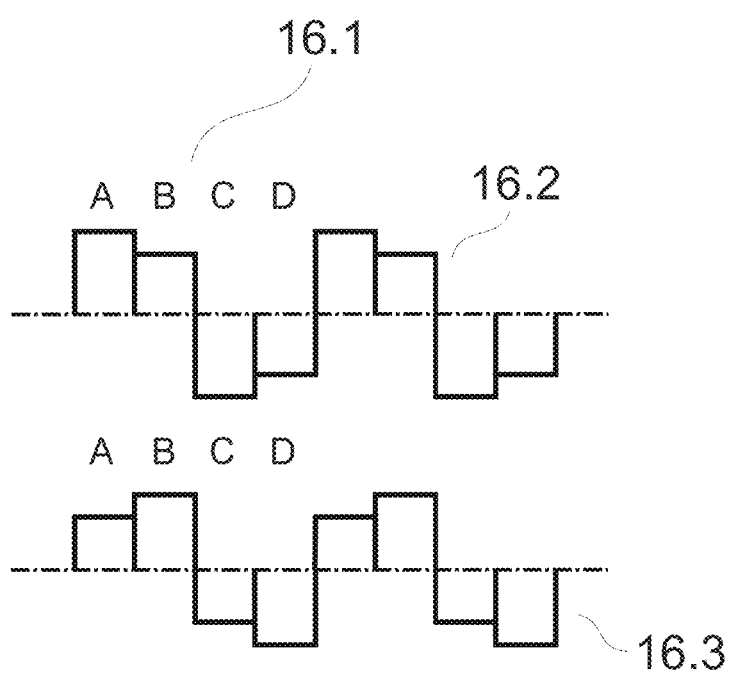
FIG. 18 illustrates the division in time of feed current segments of FIG. 16 under the influence of one or more metallic objects.
Figure 17:
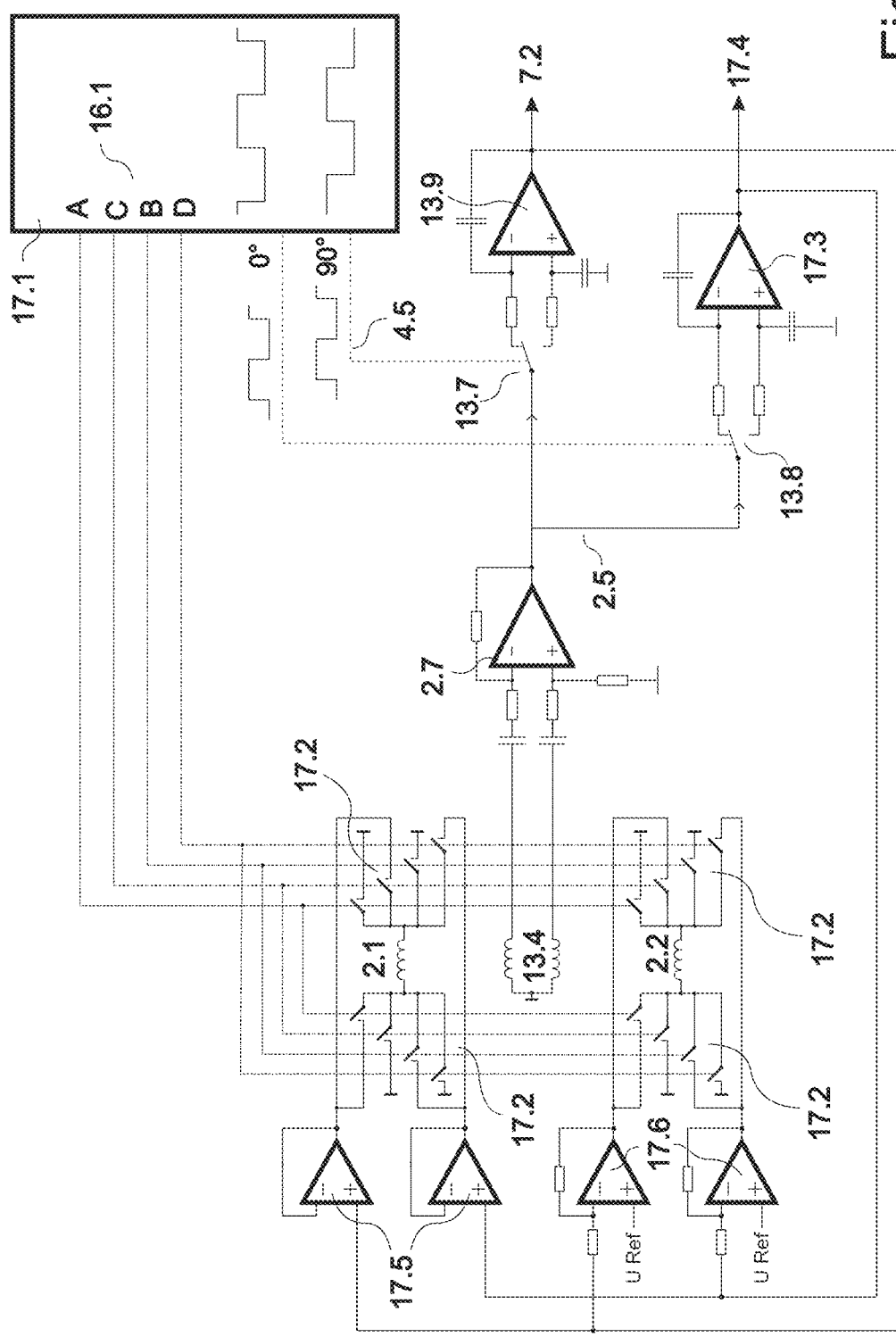
FIG. 17 illustrates a circuit diagram for detecting metallic objects according to another non-limiting embodiment.

The aim of a further exemplary embodiment which is illustrated in FIGS. 16 to 18 is to completely regulate out the output signal 2.5 which will contribute at the same time to increasing the dynamics of the system. To this end, the sending current phases are sub-divided from the previous twice 180° into four times 90°. The demodulation of the output signal 2.5 of the preamplifier 2.7 continues to occur at the rate of the demodulation clock 4.5 and the rate of the demodulation clock 4.4 which is shifted by 90° (FIG. 4). The previous feed current 2.3 or 2.4 of the transmission coil arrangement comprising 180° long segments is now sub-divided in accordance with FIG. 4 into four segments, designated by A, B, C, D each of 90°. FIG. 16 shows the division in time of the feed current segments 16.1. The clock segment C corresponds to the current through the coil in the clock segment A, whereby only the direction of the current is inverted in the coil. The same applies for the clock segments B and D. As before in FIG. 13, the current in the coils 2.1 and 2.2 continues to be regulated by the regulating value 7.2 in FIG. 17, however, only in the clock segments A and C.

The demodulation of the third demodulation phase 6.3 and the fourth demodulation phase 6.4 is effected with the second switch for the synchronous demodulation process 13.8 together with the high-gain comparator 17.3. The second regulating value 17.4 for the regulation of the coil feed currents in the clock segments B and D is now present at the output of the comparator 17.3. The coils 2.1 and 2.2 are controlled with mutually inverted regulated currents 16.2 and 16.3 by the switching arrangements 17.2 via the current driver 17.5 and the corresponding inverting current driver 17.6. The switching arrangements serve for appropriately distributing the coil currents in the clock segments 16.1.

Due to the separate regulation of the coil currents in the four clock segments A, B, C and D, the output signal 2.5 of the preamplifier 2.7 becomes a pure "zero" signal, i.e. no clock synchronous signal components at all are contained in the output signal. This applies to a measurement without as well as under the influence of metal. The output signal 2.5 of the preamplifier 2.7 thus consists only of the amplifier noise.

Preferably, without the influence of metal, coil currents of the same magnitude are established as illustrated in FIG. 16. Under the influence of metal, the coil currents differ as illustrated in FIG. 18 for example. All the information regarding the metal that is being measured is now contained in the two regulating values 7.2 and 17.4. The further processing of the signals remains the same as already described in the first exemplary embodiment.

In a third exemplary embodiment, the total coil current, i.e. the regulated coil current is regulated by the first and the inverted regulated coil current through the second coil in the clock segments A and C in proportion to the total coil current in the clock segments B and D. Generally spoken, the averaged signals from the clock segments A and C and the signals in the clock segments B and D are used in order to determine the regulating values. In this case too, the output signal 2.5 becomes a "null" signal, whereby the two regulating values 7.2 and 17.4 are again established.

It is self-evident that this description can be subjected to the most diverse modifications, changes and adjustments which fall within the range of equivalents to the accompanying Claims.

The invention claimed is:

1. A method for locating metal or metal-containing objects and materials, comprising:
   delivering at least two transmission signals to at least one receiving coil, the at least two transmission signals including a first transmission signal through a first transmission coil and a second transmission signal through a second transmission coil, the second transmission signal being inverted with respect to the first transmission signal;
   mutually regulating currents in the at least two transmission coils in such a way that average values of receiving coil output signals, received from the at least one receiving coil and generated from demodulation processes, are continuously mutually regulated to "zero" even under the influence of metal,
   wherein a first average value of the receiving coil output signal demodulated in a first demodulation process is of a same size in a stabilized state as a second average value of the receiving coil output signal, when demodulated in a further demodulation process,
   wherein amplitudes of control variables to generate a regulation to "zero" are acquired by demodulation in the first demodulation process and in the further demodulation process which contains a phase angle that is shifted by 90° relative to a phase angle of the first demodulation process, and wherein the receiving coil output signals of the first demodulation process and the receiving coil output signals of the further demodulation process are caused to be congruent by means of a multiplier determined from the control variables.

2. A method in accordance with claim 1, wherein the multiplier is set automatically by software or manually by potentiometers.

3. A method in accordance with claim 1, wherein an existing difference of the receiving coil output signal of the first demodulation process and the receiving coil output signal of the further demodulation process is mutually regulated out, the control variable determined thereby being used as a detection value for acquiring other metal objects.

4. A method in accordance with claim 1, wherein at least one of the control variables and/or the multiplier is used as a detection value for locating or masking out an object under the influence of metal.

5. A method in accordance with claim 4, wherein the detection value at which the receiving coil output signals of the first demodulation process and of the further demodulation process are congruent is stored for a specific metal, when a metal contact is present.

6. A method in accordance with claim 1, wherein the multiplier at which the receiving coil output signals of the first demodulation process and of the further demodulation process are congruent is stored for a specific metal, when a metal contact is present.

7. A method in accordance with claim 1, wherein the multiplier serving as an identifier for a particular object is compared with a value from a table which designates a detected object in plain language and is emitted as required.

8. A method in accordance with claim 1, wherein only a "learnt" object is detected whilst all other objects are masked out.

9. A method in accordance with claim 1, wherein sending current phases correspond to the demodulation processes and are sub-divided within a clock cycle into four segments A, B, C, D, the phase angle of which is 90° apart in each segment, which segments are inverted alternately or in pairs in regard to a direction of a current.

10. A method in accordance with claim 9, wherein there are determined separate regulating values associated in pairs with the segments A, C and B, D.

11. A method in accordance with claim 9, wherein a regulated coil current is regulated by a first and an inverted regulated coil current through a second coil in the segments A and C in relation to the segments B and D.

12. A method for locating metal or metal-containing objects and materials, comprising:

delivering at least two transmission signals to at least one receiving coil, the at least two transmission signals including a first transmission signal through a first transmission coil and a second transmission signal through a second transmission coil, the second transmission signal being inverted with respect to the first transmission signal;

mutually regulating currents in the at least two transmission coils in such a way that a receiving coil output signal, received from the at least one receiving coil and generated from demodulation processes, are continuously mutually regulated to "zero" even under the influence of metal, wherein the receiving coil output signal demodulated in a first demodulation process is of a same size in a stabilized state as the receiving coil output signal, when demodulated in a further demodulation process, wherein amplitudes of control variables to generate a regulation to "zero" are acquired by demodulation in the first demodulation process and in the further demodulation process which contains a phase angle that is shifted by 90° relative to a phase angle of the first demodulation process, and wherein the receiving coil output signals of the first demodulation process and the receiving coil output signals of the further demodulation process are caused to be congruent by means of a multiplier determined from the control variables.

* * * * *